United States Patent [19]

Motoyama et al.

[11] Patent Number: 4,472,960
[45] Date of Patent: Sep. 25, 1984

[54] METHOD OF AND APPARATUS FOR TESTING PROPERTIES

[75] Inventors: Shimesu Motoyama; Kaoru Kurita; Akira Iwasaki, all of Tokyo, Japan

[73] Assignee: Freund Industrial Co., Ltd., Tokyo, Japan

[21] Appl. No.: 287,687

[22] Filed: Jul. 28, 1981

[30] Foreign Application Priority Data

Aug. 6, 1980 [JP] Japan .............................. 55-107962

[51] Int. Cl.³ ........................ G01N 3/56; G01N 3/40
[52] U.S. Cl. ........................................... 73/7; 73/78;
73/432 R; 33/178 R; 364/552
[58] Field of Search ................. 73/432 G, 432 Z, 78,
73/7, 760, 432 R, 821; 177/50; 356/402, 407,
72, 73, 425; 33/178 R, 169 R; 422/50, 64;
414/224; 198/397; 364/552; 209/599

[56] References Cited

U.S. PATENT DOCUMENTS

| | | | |
|---|---|---|---|
| 3,000,331 | 9/1961 | Frank | 73/432 V |
| 3,039,604 | 6/1962 | Bickel et al. | 73/432 V |
| 3,210,552 | 10/1965 | Young | 356/407 |
| 3,254,753 | 6/1966 | Aidlin | 198/397 |
| 3,618,395 | 11/1971 | Melliger | 73/432 Z |
| 3,744,582 | 7/1973 | Withnell et al. | 177/50 |
| 3,757,566 | 9/1973 | Flary | 73/78 |
| 3,838,766 | 10/1974 | Wagers, Jr. et al. | 198/397 |
| 3,863,351 | 2/1975 | Kalen | 33/169 R |
| 4,099,239 | 7/1978 | Williams | 364/476 X |
| 4,121,289 | 10/1978 | Stiel | 364/476 X |
| 4,223,751 | 9/1980 | Ayers et al. | 177/50 |
| 4,236,413 | 12/1980 | Schmid et al. | 73/821 |
| 4,308,942 | 1/1982 | Ackley | 198/397 |
| 4,335,438 | 6/1982 | Smolen | 73/432 Z X |
| 4,353,456 | 10/1982 | Yamamoto | 198/397 |

FOREIGN PATENT DOCUMENTS 2716985 10/1978 Fed. Rep. of Germany ........ 73/760

OTHER PUBLICATIONS

*Research Disclosure,* No. 182, Jun. 1979, "Article Thickness Measurement Device", p. 306, #18223.

*Primary Examiner*—Gerald Goldberg
*Assistant Examiner*—Brian R. Tumm
*Attorney, Agent, or Firm*—Armstrong, Nikaido, Marmelstein & Kubovcik

[57] ABSTRACT

Method of and apparatus for testing required properties of the specimen solids such as tablets, pills, granules, capsules, etc. automatically and continuously. After nondestructive tests are performed, then destructive tests are performed automatically and continuously. The data obtained by the tests can be processed to record and display the processed data. The nondestructive tests comprise at least one of the tests of the weight, diameter, thickness, color difference, and surface area, etc. which are performed in order or simultaneously. The destructive tests comprise at least one of the tests of the hardness, disintegration, dissolution, abrasion and chemical analysis. The apparatus consists of supply a mechanism for supplying the solids, nondestructive test mechanisms, destructive test mechanisms and a system for transferring solids from one test position to the next test position.

9 Claims, 5 Drawing Figures

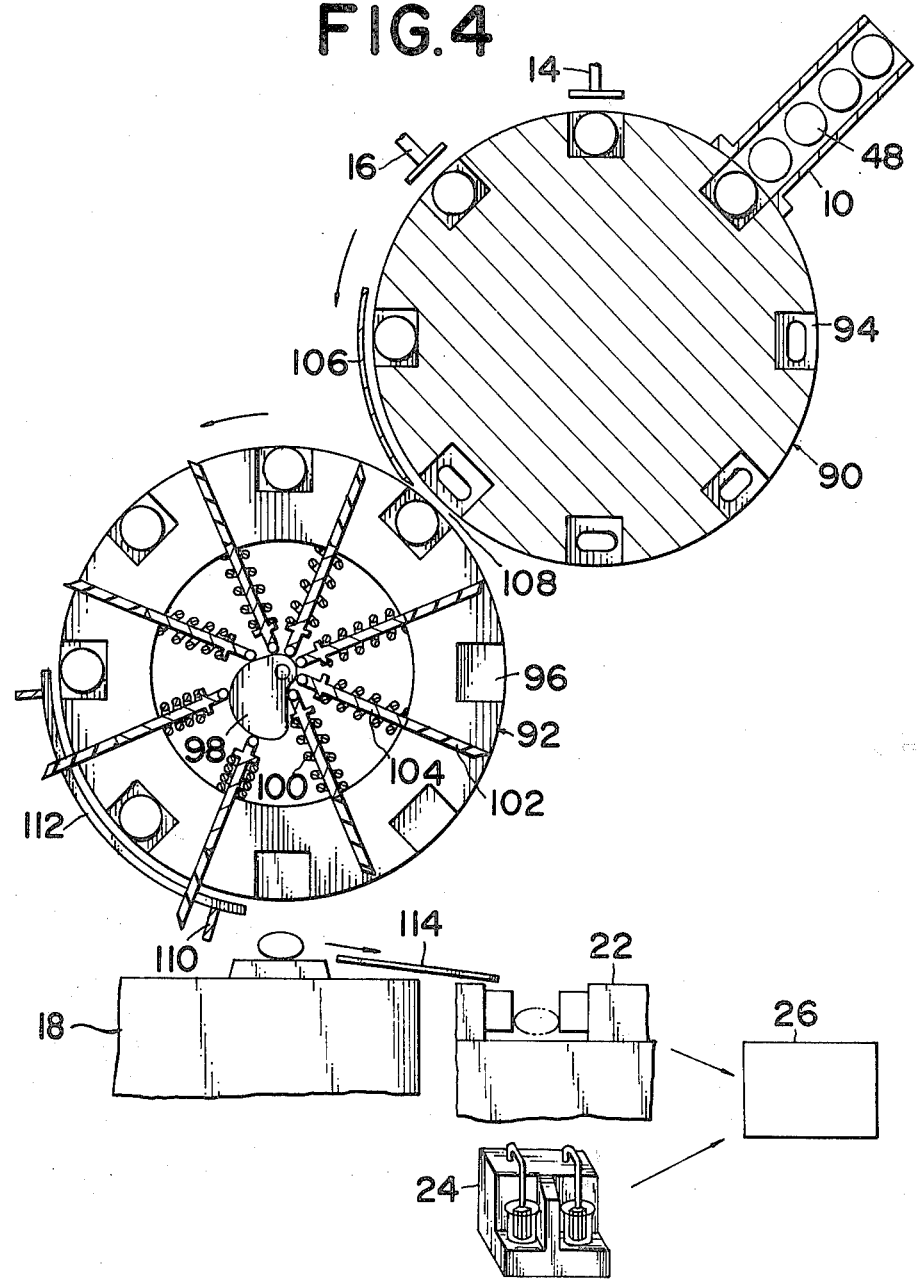

METHOD OF AND APPARATUS FOR TESTING PROPERTIES

BACKGROUND OF THE INVENTION

1. Field of the Invention

This invention relates to a method of and apparatus for testing any required properties of pharmaceutical solids such as tablets, pills, granules, and capsules etc. automatically and continuously.

2. Prior Art

In recent years, a standard relating to manufacture and quality control of pharmaceutical goods, called GMP (Good Manufacturing Practice) has been enacted in many countries. GMP specifies, because of the importance of pharmaceutical goods which can decide one's life, that it is required to make quality control such as chemical analysis, to maintain optimum equipments and environments for manufacturing pharmaceutical goods, and to take care of all manufacturing practices including manufacture, packaging, display, and storage of pharmaceutical products and materials.

To make GMP effective, there are many detailed provisions in the Japanese pharmacopoeia with regards to weight deviation and disintegration, etc. Further, it is usual to test the hardness and abrasion of tablets and to measure thickness and diameter, etc. of the tablets so as to prevent administered amount of medicine from becoming inaccurate by reasons of destruction and abrasion during manufacture, conveyance and medication. These tests can be divided into two groups. One of which is a nondestructive test which gives no change to pharmaceutical solid such as tablet, and the other is a destructive test which provides gives certain changes such as division, crushing, dissolution or abrasion to pharmaceutical solid. Usually, nondestructive test includes measurements of weight, diameter and thickness, while destructive test includes measurements of hardness and disintegration.

In one of the prior practices, above tests have been made by allotting more than one person to each test and proceeding each test separately. In another prior practice, only one person is carrying out several different tests one by one.

Therefore, most of above prior arts require plural persons and long testing time, and are therefore expensive. Further, since the prior tests depend considerably on personal experience and dexterity, the results of tests may include personal deviations to such extent that precise test data cannot be expected.

SUMMARY OF THE INVENTION

Accordingly, it is a general object of the present invention to provide a method of and apparatus for testing properties of solids, wherein exact tests can be carried out automatically, continuously and economically without personal errors or deviations.

In the method of the present invention, nondestructive tests are made at first and then destructive tests are made continuously and automatically.

The apparatus of the present invention includes means for supplying specimen solids, means for performing nondestructive tests, means for performing destructive tests on the solids, and means for transferring the solids from one test position to the next position.

According to the another aspect of the present invention, the data obtained as the results of the tests are automatically processed to be recorded and displayed.

The nondestructive tests include measurements of weight, diameter, thickness, color difference, surface area, etc. The destructive tests include measurements of hardness, disintegration, dissolution, and abrasion and chemical analysis, etc. The results of the tests can be printed out and displayed by a printer and display instrument, not only measurement values but also the mean values and standard deviations obtained by the data processor from the measured values in accordance with an automated statistical analysis.

BRIEF DESCRIPTION OF THE DRAWINGS

The above and other objects and features of the present invention will become more apparent when referred to the following descriptions stated in conjunction with the accompanying drawings, wherein like reference numerals denote like elements and in which:

FIG. 4 is a diagrammatical sectional view of a third embodiment of the present invention.

DETAILED DESCRIPTION OF THE PREFERRED EMBODIMENTS

Figure 1:
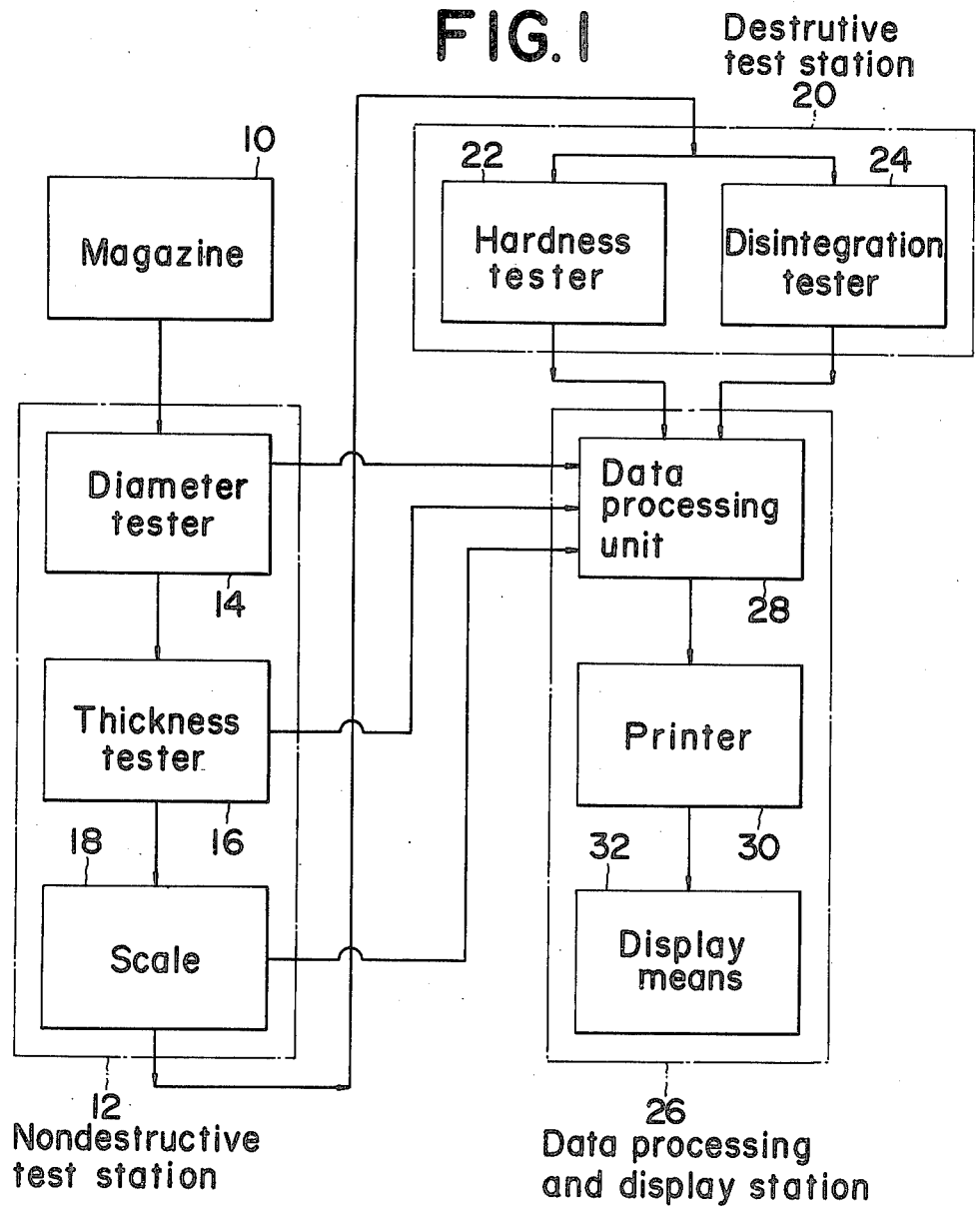
FIG. 1 is a block diagram showing an example of the principle of the present invention.

Referring now to the drawings, FIG. 1 shows a block diagram according to an example of the principle of the present invention, wherein reference numeral 10 is a magazine for setting a predetermined number of pharmaceutical solids, for example, twenty tablets and supplying them one by one. Reference numeral 12 denotes a nondestructive test station for testing tablets without giving any physical and chemical changes. The nondestructive test station 12 includes a diameter tester 14 for measuring the diameter of the tablet one by one, a thickness tester 16 for measuring the thickness of the tablet, and a scale 18 for measuring the weight of the tablet. The arrangement order of said measuring devices 14, 16, and 18 is not limited to that shown in FIG. 1, but it is possible to arrange them in other serial order or parallel order. Namely, in one example, tester 16 can be arranged in the first, or all of the measuring means 14, 16, 18 can be arranged in parallel order to perform all measurements simultaneously. Further, said nondestructive test station 12 may include other nondestructive test means, for example, means for measuring color difference and/or surface area of a tablet. These additional measuring devices may also be arranged in serial or parallel order.

Arranged at the downstream of said nondestructive test station 12 is a destructive test station 20 for testing tablets by giving some changes such as division or abrasion, etc. to the tablets. The destructive test station 20 includes, in the illustrated embodiment, a hardness tester 22 for measuring hardness of the tablet and a disintegration tester 24 for measuring disintegration of the tablet. Although the illustrated testers 22 and 24 are arranged in parallel, it is possible to omit one of them, or provide in parallel or serial order, other destructive test devices such as a dissolution tester, an abrasion tester, or chemical analysis devices for performing qualitative tests, quantitative tests or identification tests, etc.

At the downstream of said destructive test station 20, a data processing and display station 26 is provided. This station 26 processes statistically the data of the results of the tests obtained at said nondestructive and destructive test stations 12 and 20 so as to print out and display the obtained data. The station 26 includes a data processing unit 28, a printer 30 for printing out the processed data sent from the data processing unit 28, and display device 32 for displaying the processed data. Said data processing unit 28 is connected with said diameter tester 14, thickness tester 16, scale 18, hardness tester 22, and disintegration tester 24 in order to process statistically the data sent from said test devices 14, 16, 18, 22 and 24 to calculate the mean value and standard deviation based on the measurement data in accordance with any control system, such as x-R control chart system of JIS (Japanese Industrial Standard).

Figure 2:
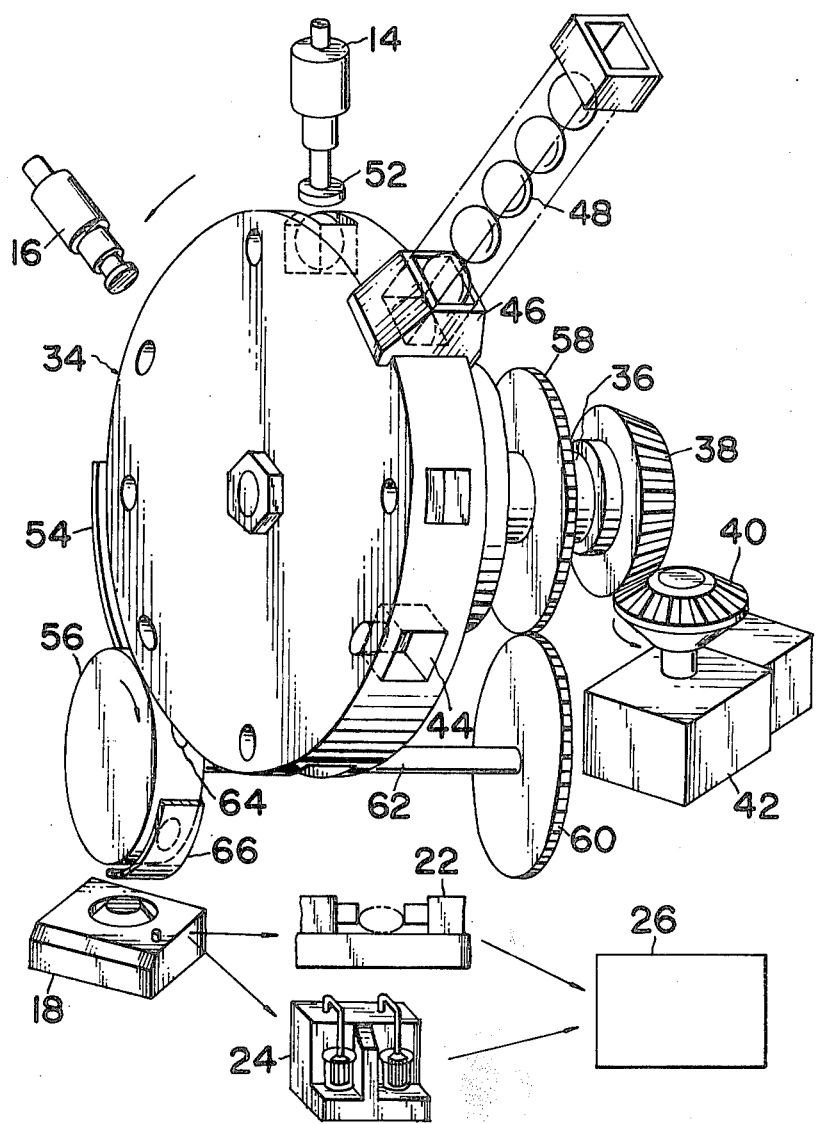
FIG. 2 is a diagrammatical perspective view of the apparatus in accordance with a first embodiment of the present invention.

FIG. 2 is a diagrammatical perspective view of the apparatus according to the first embodiment of the present invention. The apparatus of this embodiment includes a rotary drum 34 having a rotatable shaft 36 connected to a driving motor (not shown) via two bevel gears 38, 40 and a divider 42 so as to be rotated by the driving motor through every rotary motion divided into eight equidistant segments by the divider 42. Also, around the outer periphery of the rotary drum 34 of this embodiment, eight recesses 44 for holding the tablet are provided equidistantly.

A magazine holder 46 is provided at a portion of the outer periphery of the rotary drum 34, and has the magazine 10 for holding a number of specimen, for example about twenty of tablets, The magazine 10 supplies the tablet 48 into a holder 52 held in the recess 44, one by one. The holder 52 can be replaced depending upon the size of the tablet 48.

At the downstream of the rotational direction of the drum 34, there is provided a diameter tester 14 for measuring the diameter of the tablet 48 held in the holder 52 and fed through the rotation of the rotary drum 34. The diameter tester 14 has a construction which measures the diameter of the tablet 48 by contacting directly with the outer periphery of the tablet 48 from outside direction. The diameter tester 14, may, however, be other type of tester such as a photoelectric sensor which is able to measure the diameter of the tablet 48 without contacting it.

At the downstream of the rotational direction of the rotary drum 34, a thickness tester 16 for measuring the thickness of the tablet 48 is provided. The thickness tester 16 measures the diameter of the tablet 48 by contacting with or without contacting the tablet 48. For example, it is possible to measure the thickness by using a photoelectric sensor or a system which detects the thickness as the angle corresponding to it and converts the angle into the thickness to display it in digital form.

Positioned at the diametrically opposite position of the drum 34 to the magazine 10 is a rotor 56. The rotor 56 receives from the holder 52 the tablet 48 fed from the thickness tester 16 with the aid of a guide plate 54 which prevents the tablet 48 from dropping out of the holder 52, and conveys the tablet 48 onto a scale 18 which measures the weight of the tablet 48. The rotor 56 is rotatable by a shaft 62 having a gear 60 which meshes with a gear 58 mounted on the rotatable shaft 36 of the drum 34 so that the rotor 56 can be rotated synchronously with the rotary drum 34.

Around the outer periphery of the rotor 56, there are provided a plurality of recesses 64 for receiving and holding the tablet 48 from the holder 52. The distance between each recess 64 is equal to that between each recess 44 of the drum 34. A guide plate 66 which prevents the tablet 48 from dropping out of the recess 64 is positioned at the right (FIG. 2) of the rotor 56. Alternatively, the rotor 56 may be consisted of an usual funnel-shaped chute etc.

The scale 18 for measuring the tablet 48 dropped down from the recess 64 of the rotor 56 is provided beneath the rotor 56. The scale 18 may be a conventional weighing apparatus or a digital scale using light emitting diode (LED) etc.

At the downstream (or right in FIG. 2) of the scale 18, a hardness tester 22 for measuring hardness of the tablet 48 fed from the scale 18 by a cylinder (not shown), and a disintegration tester 24 for measuring the disintegration of the tablet 48 are provided in parallel order. The hardness tester 22 may be one using a differential transformer or a strain gauge, or a Monsant type hardness tester.

Further, although not shown in detail in FIG. 2, said diameter tester 14, thickness tester 16, scale 18, hardness tester 22, and disintegration tester 24 are connected to the data processing display station 26.

The operation of said apparatus is set forth in the following. At first, for example, twenty of tablets 48 are set into the magazine 10. When the rotary drum 34 is rotated counterclockwise by every one-eighth of rotation by means of the driving motor (not shown) through the divider 42, the bevel gear 40, 38, and the rotatable shaft 36, each tablet 48 drops down one by one, into the holder 52 held in the recess 44 and then is fed to the diameter test station, wherein the diameter of the tablet 48 is measured by the diameter tester 14. The data obtained is transmitted to the data processing unit 28. After the measurement of the diameter is completed, by one-eighth rotation of the rotary drum 34, the tablet 48 is fed to the thickness test station, wherein the thickness of the tablet 48 is measured and the data obtained is transmitted to the data processing unit 28. During this time, the next tablet 48 is fed to the diameter test station, in which the measurement of the diameter by the diameter tester 14 and the transmission of the measurement data to the data processing unit 28 are proceeded. After the measurement of the thickness is over, the rotary drum 34 is rotated in two steps of one-eighth, namely one-fourth in total, thereby said first tablet 48 is dropped down from the holder 52 into the recess 64 of the rotor 56. Since the rotor 56 is rotated in synchronism with the rotary drum 34, the tablet 48 is dropped down from the recess 64 onto the scale 18, by which the weight of the tablet 48 is measured and the data obtained is transmitted to the data processing unit 28. During this time, both of the diameter test station and the thickness test station are supplied with tablets 48 one by one at every one-eighth rotation of the rotary drum 34 to measure the diameter and the thickness of the tablet. When the measurement of the weight is over, the nondestructive test in this embodiment is completed.

Next to the above nondestructive test, the destructive test is proceeded continuously. Namely, after the weight of the tablet 48 is measured, the tablet 48 is fed to one of the hardness tester 22 and the disintegration tester 24 by a feeding device such as a cylinder (not shown). The hardness tester 22 measures the hardness of the tablet 48, and the data obtained by the measurement is transmitted to the data processing unit 28. On the other hand, if the tablet 48 is fed to the disintegration tester 24, the tester 24 measures the disintegration of the tablet 48 according to the standard practice of the pharmacopoeia in a test vessel which is filled with a test liquid such as artificial gastric juice, and the data obtained is transmitted to the data processing unit 28.

The data processing unit 28 processes statistically the data transmitted from the diameter tester 14, thickness tester 16, scale 18, hardness tester 22, and disintegration tester in accordance with a control system, such as the x-R control chart system of JIS to obtain the mean value, standard deviation, and the scope of value etc. The results of the measurements and the data processing are printed out by the printer 30 and displayed on the display device 32.

Further, the test results may be displayed directly on respective tester.

Figure 3A:
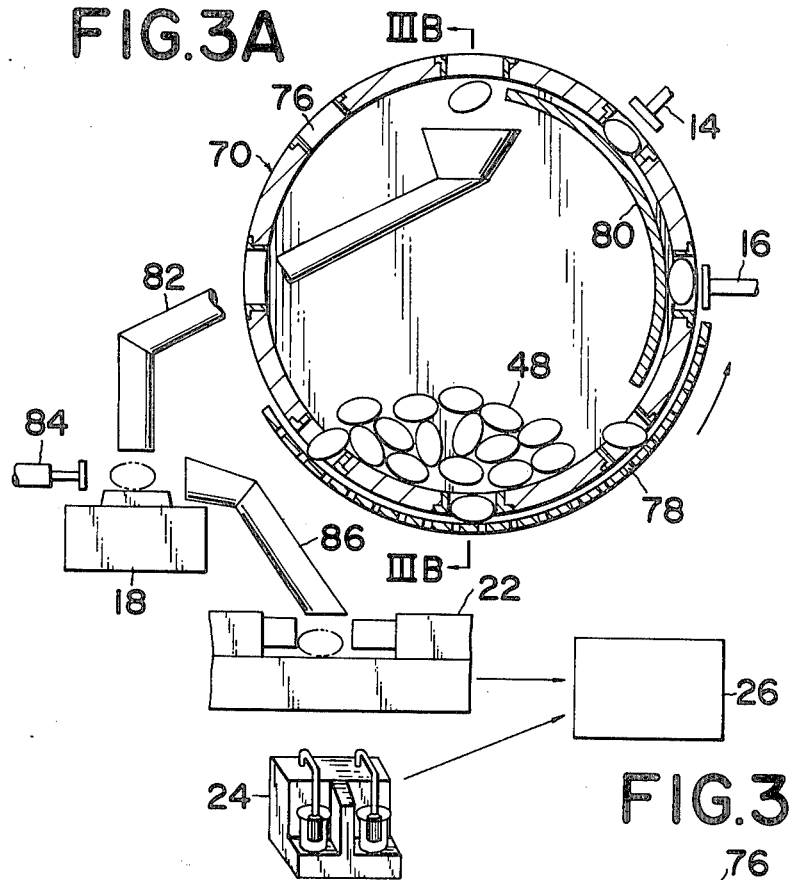
FIG. 3A is a diagrammatical sectional view of a second embodiment of the present invention.
Figure 3B:
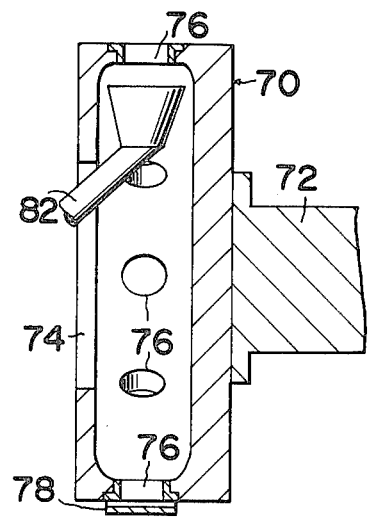
FIG. 3B is a partial sectional view along the lines IIIB—IIIB of the FIG. 3A.

FIGS. 3A and 3B show a second embodiment of the apparatus for testing properties of solids in accordance with the present invention. This embodiment includes a hollow rotary drum 70 which is connected to a divider and a driving morot (not shown) via a rotatable shaft 72. The rotary drum 70 has at a side opposite to the rotatable shaft 72 an opening 74, through which the specimen tablets 48 are supplied into the hollow drum 70. The rotary drum 70 has also at the outer periphery eight apertures 76 for holding the tablets 48, perforated equidistantly in the circumferential direction.

In this embodiment, as the hollow rotary drum 70 is which a number of tablets 48 are supplied through the opening 74 is rotated at every one-eighth rotation, the tablets 48 are dropped into the apertaure 76 one by one and conveyed in the counterclockwise direction as shown by an arrow with the guide of an outer guide plate 80 arranged at the outside of the drum 70, and then the tablet 48 is guided by an inner guide plate 80 positioned inside of the drum 70. When the tablet 48 arrives at the thickness test station, the diameter of the tablet 48 is measured by the thickness tester 16. After this measurement is over, the tablet 48 arrives at the diameter tester 14 by the next one-eighth rotation of the rotary drum 70 in order to measure the diameter of the tablet 48. Thereafter, as the drum 70 is rotated, the tablet 48 reaches to the upper limit of the drum 70 at which the tablet 48 is dropped down from the aperture 76 through a chute 82 onto the scale 18. When the weight of the tablet 48 is measured by the scale 18, the nondestructive test is completed.

Then, tablet 48 is fed by a cylinder 84 from the scale 18 onto the hardness tester 22 of the destructive test station through a chute 86 so as to measure the hardness of the tablet 48. On the other hand, the next tablet 48 is fed through another chute (not shown) to the disintegration tester 24 in order to measure the disintegration of the tablet 48. The data obtained by each test is transmitted to the data processing and display station 26 to process statistically to print out and display the processed data.

In this embodiment, it is also possible to perform a plurality of property tests of the tablet 48 automatically and continuously.

FIG. 4 shows a third embodiment of the apparatus according to the present invention, in which a pair of rotary drum 90 and 92 having same diameter and rotated at the same rotational speed with each other by the same driving source. Formed respectively at the outer peripheries of the both rotary drum 90 and 92, are eight recesses 94 and 96 for holding tablet 48, these recesses 94 and 96 are arranged equidistantly in the circumferential direction. Therefore, each of the recesses 94 and 96 is aligned with each other. The rotary drum 92 is formed by joining together a pair of doughnut-shaped rings, and eight pins 104 each of which having a shock absorber 102 which is protruded and withdrawn in the radial direction against the resilient force of a compression spring 100 by an eccentric cam 98 positioned at the center of the drum 92.

In this embodiment, the tablet 48 held in the magazine 10 is dropped into the recess 94 one by one at every one-eighth rotation of the rotary drum 90 and measured the diameter and thickness thereof by each of the diameter and thickness testers respectively. Thereafter, the tablet 48 is fed with the guidance of a guide plate 106 and delivered from the recess 94 to the recess 96 by gravity. Then, the tablet 48 is fed by the counterclockwise rotation of the rotary drum 92 while being guided by a split-type guide 112 combined by connectors 110, and at the lowermost position of the drum 92, dropped down onto the scale 18 in order to measure the weight of the tablet 48. After the measurement of weight, the tablet 48 is forced, by the shock absorber 102 at the free end of the pin 104 protruded outwardly by the cam 98, toward an inclined slide plate 114 and slides down along the inclined slide plate onto the hardness tester 22 so as to measure the hardness of the tablet 48. If desired, another tablet 48 is able to be fed to the disintegration tester 24 through another inclined slide plate or a chute (not shown) in order to perform the disintegration test. The data obtained by said tests are processed statistically at the data processing and display station 26 to print out and display the processed data.

In this embodiment, therefore, it is possible to perform the nondestructive and destructive tests automatically and continuously.

As apparent from the foregoing detailed description, according to the present invention, it is possible to perform the property test rapidly and exactly at low cost. Further, it is also possible to obtain highly usable test data promptly by processing the test automatically so as to print out and display the processed data.

While some preferred embodiments of the present invention are described herein in detail, it is to be understood that the present invention is not limited thereby and many other modifications can be made within the spirit and scope of the attached claim.

What is claimed is:

1. An apparatus for testing properties of a pharmaceutical solid including at least one of a tablet and pill, comprising means for supplying the solid, a rotary drum rotatable in a vertical plane and having at the outer periphery recesses for holding said solid supplied one by one from said supply means, means for guiding said solid transferred by said rotary drum, means for performing at least one nondestructive test on said solid supplied from said supply means and located peripherally adjacent said rotary drum, means for performing a destructive test on said solid fed from said nondestructive test means, means for processing the data obtained by said tests automatically in one processing unit, means for recording said processed data, and means for displaying said processed data.

2. An apparatus according to claim 1, wherein said nondestructive test means include at least one of means for measuring the weight, diameter, thickness, and surface area of said solid, which are arranged in series or parallel.

3. An apparatus according to claim 1, wherein said destructive test means include at least one of means for measuring the hardness, disintegration, dissolution, abrasion, and chemical analysis of said solid.

4. An apparatus according to claim 1, wherein the data obtained by said data processing means includes the measurement values, and calculating mean values and standard deviations.

5. an apparatus according of claim 1, wherein said rotary drum comprises a hollow drum in which said solid is held, said hollow drum having apertures which hold said solid one by one, and means arranged along portions of outer and inner walls of said hollow drum for guiding said solid.

6. An apparatus according to claim 1, wherein said at least one of said means for performing a nondestructive test and destructive test on said solids is a test means for measuring the diameter of the solid.

7. An apparatus according to claim 1, wherein said transferring means includes a cam and a shock absorber which operate together to transfer said solid from said means for performing a nondestructive test to one of said means for performing a nondestructive test and destructive test on said solid.

8. an apparatus according to claim 1, wherein said rotary drum comprises a pair of rotary drums which deliver said solid from one to the other while being rotated in each of the opposite directions.

9. An apparatus according to claim 1, including at least three means for performing nondestructive tests.

* * * * *